United States Patent
Dumoulin et al.

(10) Patent No.: US 7,787,935 B2
(45) Date of Patent: *Aug. 31, 2010

(54) SYSTEM AND METHOD FOR CORRECTING MOTION ARTIFACTS IN IMAGING

(75) Inventors: Charles Lucian Dumoulin, Ballston Lake, NY (US); Robert David Darrow, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 1246 days.

This patent is subject to a terminal disclaimer.

(21) Appl. No.: 10/951,300

(22) Filed: Sep. 27, 2004

(65) Prior Publication Data

US 2006/0074296 A1     Apr. 6, 2006

(51) Int. Cl.
*A61B 5/05* (2006.01)

(52) U.S. Cl. .................... 600/427; 600/410; 600/411; 600/413; 600/428; 324/307; 324/309; 324/318

(58) Field of Classification Search .............. 600/410, 600/427, 424, 428, 429, 411, 413; 324/307, 324/309, 318

See application file for complete search history.

(56) References Cited

U.S. PATENT DOCUMENTS

| 5,271,400 | A | | 12/1993 | Dumoulin et al. ......... 128/653.2 |
| 5,318,025 | A | * | 6/1994 | Dumoulin et al. ........... 600/417 |
| 5,577,502 | A | * | 11/1996 | Darrow et al. .............. 600/426 |
| 5,947,900 | A | * | 9/1999 | Derbyshire et al. ......... 600/410 |
| 6,275,721 | B1 | * | 8/2001 | Darrow et al. .............. 600/410 |
| 6,289,233 | B1 | * | 9/2001 | Dumoulin et al. ........... 600/410 |
| 6,879,760 | B2 | * | 4/2005 | Griffioen et al. ............ 385/100 |

* cited by examiner

*Primary Examiner*—Long V Le
*Assistant Examiner*—Ellsworth Weatherby
(74) *Attorney, Agent, or Firm*—Jason K. Klindtworth

(57) ABSTRACT

A method for tracking a device used in an imaging system is provided. The method includes using a trigger for initiating a determination of multiple device locations. The scan parameters are then adjusted using the multiple device locations. Finally, a dynamically corrected image is acquired, where the adjusted scan parameters provide an offset for at least one scan parameter.

22 Claims, 5 Drawing Sheets

SYSTEM AND METHOD FOR CORRECTING MOTION ARTIFACTS IN IMAGING

BACKGROUND OF THE INVENTION

The present invention relates generally to the field of device tracking for medical imaging. In particular, the invention relates to methods and systems for correcting motion artifacts in imaging applications using device tracking.

Several imaging techniques for example, X-ray fluoroscopy, Computed Tomography (CT), Ultrasound, and Magnetic Resonance (MR) imaging employ the use of a device placed inside or on the patient during diagnostic, therapeutic or surgical medical procedures. These procedures typically take a long time resulting in inconvenience and the possibility of exposure to extra dosage in case of X-rays. MR imaging eliminates the dosage issue but it has been most successful in applications in which motion is minimal. Since the frame of reference in the MR scanner is the gradient coil system, small changes in the position of anatomy cause image blurring. This is particularly problematical for small Field-of-View (FOV) imaging where small motions can move MR signal sources over a substantial portion of the image.

MR imaging poses special challenges for acquisition of high-quality images from a vessel wall for example a blood vessel wall inside the patient. To maximize the Signal-to-Noise Ratio (SNR), intravascular imaging coils are frequently used. In vessels such as the coronary arteries, however, this SNR gain is overshadowed by the extreme motion caused by the cardiac cycle and respiration. There is a clear need for imaging strategies that can overcome this limitation.

MR tracking has been used for several years to control the imaging plane of the scanner. This technique has been called "Guided Scan" and has proven very successful for applications as diverse as dynamic joint imaging and vascular localization. With this method a device (e.g. a catheter) is located and the measured coordinates are immediately used to control the scan plane location of one or more subsequent images. Although the localization is relatively fast, patient or anatomic motion during image acquisition can result in severe image artifacts.

There is a continuing need, therefore, for improvements in device tracking techniques that address motion artifacts in image acquisition.

SUMMARY OF THE INVENTION

According to one aspect of the present technique, a method for tracking a device used in an imaging system is provided. The method includes using a trigger for determining multiple device locations. The scan parameters are then adjusted using the multiple device locations. Finally, a dynamically corrected image is acquired, where the adjusted scan parameters provide an offset for at least one scan parameter.

According to another aspect of the present technique, an imaging system is provided that uses a device for receiving a plurality of signals from an anatomy of interest. The imaging system also includes a control and acquisition circuit for initiating the detection of a plurality of device locations and for adjusting scan parameters using the plurality of device locations. The imaging system further includes a system controller circuit for acquiring a dynamically corrected image, where the scan parameters are adjusted to provide an offset for at least one scan parameter. According to aspects of the present technique, the anatomy of interest undergoes a periodic or a non-periodic motion.

DETAILED DESCRIPTION OF SPECIFIC EMBODIMENTS

Figure 1:
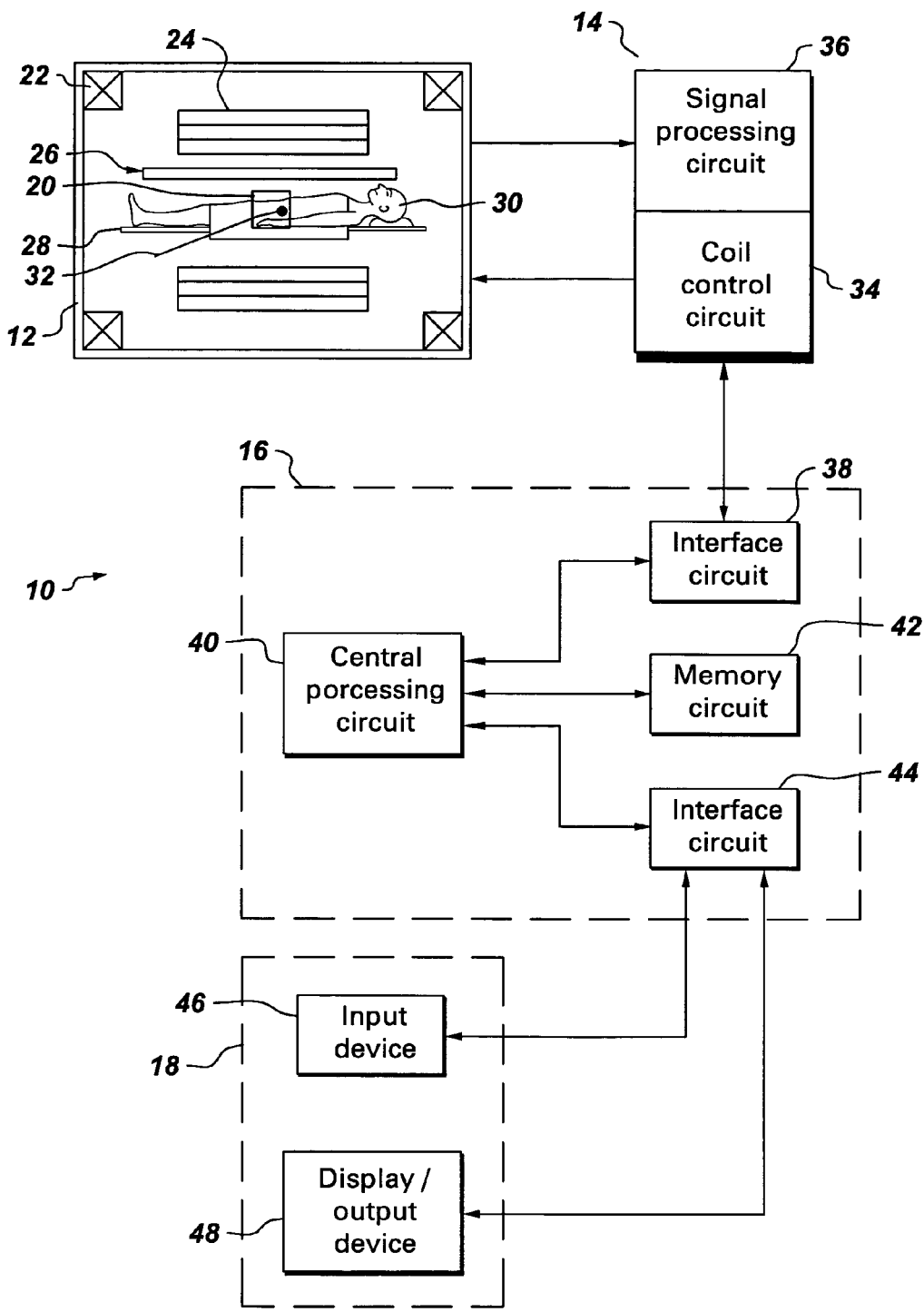
FIG. 1 is a schematic block diagram of an exemplary magnetic resonance (MR) imaging system suitable for use with the present techniques.

Referring now to FIG. 1, a magnetic resonance system, designated generally by the reference numeral 10, is illustrated as including a magnet assembly 12, a control and acquisition circuit 14, a system controller circuit 16, and an operator interface station 18. The magnet assembly 12, in turn, includes coil assemblies for selectively generating controlled magnetic fields used to excite gyromagnetic materials spin systems in a subject of interest. In particular, the magnet assembly 12 includes a primary coil 22, which will typically include a superconducting magnet coupled to a cryogenic refrigeration system (not shown). The primary coil 22 generates a highly uniform B0 magnetic field along a longitudinal axis of the magnet assembly. A gradient coil assembly 24 consisting of a series of gradient coils is also provided for generating controllable gradient magnetic fields having desired orientations with respect to the anatomy or region of interest 20. In particular, as will be appreciated by those skilled in the art, the gradient coil assembly produces fields in response to pulsed signals for selecting an image slice, orienting the image slice, and encoding excited gyromagnetic material spin systems within the slice to produce the desired image. In Spectroscopy systems these gradient fields may be used differently. An RF transmit coil 26 is provided for generating excitation signals that result in MR emissions from a subject 30 that are influenced by the gradient fields, and collected for analysis as described below. According to aspects of the present technique, a device 32 may be inserted or optionally disposed near the anatomy of interest 20 of the subject 30. The device 32 maybe a guidewire, a catheter, an endoscope, a laparoscope, a biopsy needle, a hand-held device or any other similar device. If desired, the device 32 may incorporate one or more radiofrequency (RF) coils. The device 32 receives the MR signals generated from the anatomy of interest 20 and the signals are collected for analysis as described below.

A table 28 is positioned within the magnet assembly 12 to support a subject 30. While a full body MRI system is illustrated in the exemplary embodiment of FIG. 1, the technique described below may be equally well applied to various alternative configurations of systems and scanners, including smaller scanners and probes used in MR applications.

In the embodiment illustrated in FIG. 1, the control and acquisition circuit 14 includes coil control circuit 34 and signal processing circuit 36. The coil control circuit 34 receives pulse sequence descriptions from the system controller 16, notably through an interface circuit 38 included in the system controller 16. As will be appreciated by those skilled in the art, such pulse sequence descriptions generally include digitized data defining pulses for exciting the coils of the gradient coil assembly 24 during excitation and data acquisition phases of operation. Fields generated by the transmit coil assembly 26 excite the spin system within the subject 30 to cause emissions from the anatomy of interest 20. Such emissions are detected by device 32 and are filtered, amplified, and transmitted to signal processing circuit 36. Signal processing circuit 36 may perform preliminary processing of the detected signals, such as amplification of the signals and determines multiple locations for the device 32 according to aspects of present technique described in more detail with respect to FIG. 2. Following such processing, the amplified signals are transmitted to the interface circuit 38 for further processing.

In addition to the interface circuit 38, the system controller 16 includes central processing circuit 40, memory circuit 42, and interface circuit 44 for communicating with the operator interface station 18. In general, the central processing circuit 40, which will typically include a digital signal processor, a CPU or the like, as well as associated signal processing circuit, commands excitation and data acquisition pulse sequences for the magnet assembly 12 and the control and acquisition circuit 14 through the intermediary of the interface circuit 38. The central processing circuit 40 also processes image data received via the interface circuit 38, to perform 2D Fourier transforms to convert the acquired data from the time domain to the frequency domain, and to reconstruct the data into a meaningful image. The memory circuit 42 serves to save such data, as well as pulse sequence descriptions, configuration parameters, and so forth. The interface circuit 44 permits the system controller 16 to receive and transmit configuration parameters, image protocol and command instructions, and so forth.

The operator interface station 18 includes one or more input devices 46, along with one or more display or output devices 48. In a typical application, the input device 46 will include a conventional operator keyboard, or other operator input devices for selecting image types, image slice orientations, configuration parameters, and so forth. The display/output device 48 will typically include a computer monitor for displaying the operator selections, as well as for viewing scanned and reconstructed images. Such devices may also include printers or other peripherals for reproducing hard copies of the reconstructed images.

Figure 2:
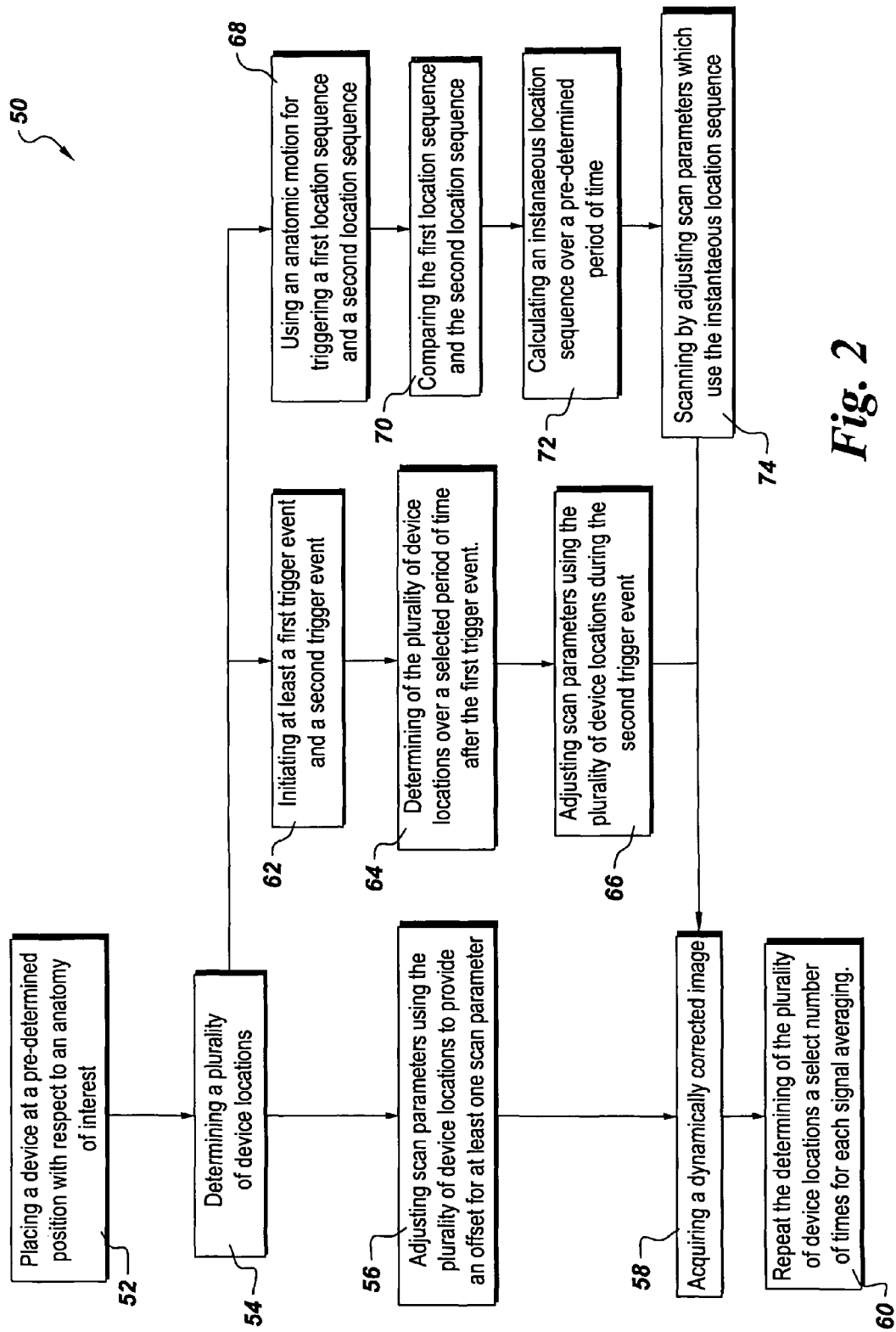
FIG. 2 is a flow-chart illustrating an exemplary device tracking method according to aspects of the present technique for use in the system of FIG. 1.

FIG. 2 is a flow-chart illustrating an exemplary device tracking method, designated generally by reference numeral 50, according to aspects of the present technique for use in the system of FIG. 1. The method includes at step 52, placing the device 32 at a pre-determined position with respect to the anatomy of interest 20 as described hereinabove. At step 54, in an exemplary embodiment, a trigger is used for initiating a determination of multiple locations for the device 32. The trigger may be a physiologic trigger like cardiac trigger, respiratory trigger, motion detection trigger, or an external trigger that also uses anatomic motion (e.g. a mechanical actuator, moving table, computer controlled trigger). Specific techniques may be employed based on whether the trigger is physiologic or external and will be described in more detail below. At step 56, the scan parameters used for image acquisition are adjusted using the multiple device locations according to aspects of present technique. At step 58, a dynamically corrected image is acquired using the adjusted scan parameters from step 56 to provide an offset for at least one scan parameter. At step 60, the method may optionally include repeating the step 54, i.e. repeating determining of the plurality of device locations a select number of times for signal averaging. This provides greater accuracy and precision in measurement of the device locations. Yet another technique for adjusting scan parameters includes comparing the multiple device locations to a pre-determined threshold. The image acquisition is suspended when a device location from the multiple device locations goes beyond the pre-determined threshold. It would be well appreciated by those skilled in the art, that the dynamically corrected image acquired by the steps described herein, is corrected for scan parameters including phase, frequency, slice offsets on a TR by TR basis, thus each acquisition results in corrected phase, frequency and slice offsets. TR is the repetition time in MR imaging, which is the time over which a basic pulse sequence is repeated to acquire all the necessary imaging lines.

The method steps as described hereinabove may be used when the anatomy of interest undergoes a periodic motion for example heart, lungs or alternatively when the anatomy of interest undergoes non-periodic motion, for example muscle motion. In embodiments of non-periodic motion, a trigger is not necessary.

Figure 3:
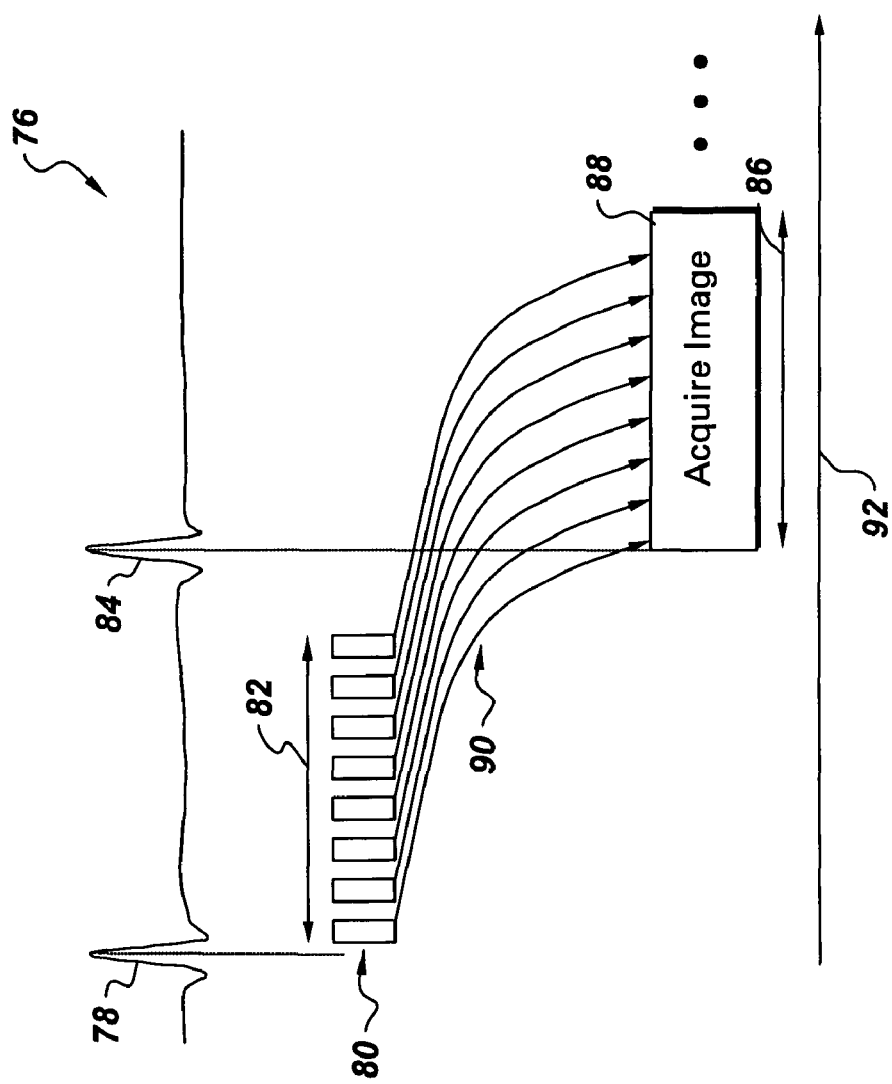
FIG. 3 is a diagrammatical representation illustrating one aspect of the method of FIG. 2 using a physiologic trigger to initiate the determination of the device location.

One aspect of the above technique described in more detail herein below with respect to FIG. 3, is when the trigger is a physiologic trigger associated with periodic motion of anatomy. In this aspect, as illustrated at step 62, the method includes initiating at least a first trigger event and a second trigger event. Multiple device locations are then determined over a selected period of time after the first trigger event at step 64. At step 66 the scan parameters are adjusted using the multiple device locations during the second trigger event. Thus in this aspect adjusting scan parameters allows obtaining a dynamically corrected image location, during the second trigger event.

In another example as illustrated at step 68, and described in more detail herein below with respect to FIG. 4, the trigger includes an external trigger as described herein above using the periodic anatomic motion, for example a cardiac motion, for triggering a first location sequence and a second location sequence. At step 70 the first location sequence and the second location sequence are compared. At step 72 an instantaneous location sequence is calculated using the compared values from the step 70 over a pre-determined period of time. At step 74 scanning is completed, by adjusting the scan parameters by using the instantaneous location sequence, and a dynamically corrected image is obtained.

The multiple device locations as described herein above include at least a horizontal and a vertical co-ordinate of the device. In a specific example the multiple device locations additionally include an orientation co-ordinate of the device, thus providing more accurate offsets of scan parameters during image acquisition. FIG. 3 and FIG. 4 further illustrate the methods steps 62-66 and 68-74 respectively of FIG. 2 in a diagrammatic form.

As described herein above, the device 32 is placed in or near the anatomy of interest. FIG. 3 and FIG. 4 illustrate schematically time diagrams 76 and 94 respectively, showing the use of multiple device locations collected using a physiologic trigger and an external trigger respectively, to offset scan parameters during actual image acquisition. In FIG. 3, multiple device locations 80 are determined over a selected period, designated generally by reference numeral 82, after a trigger event 78. The trigger events may include detection of the R-wave in the cardiac cycle, detection of breathing motion, which may be sensed by a sensor on the abdomen, or other stimulus periodic movement. The period 82 can be longer than the period of the trigger event (e.g. tracking over multiple heart beats) if desired. Once a series of device locations has been measured responsive to a trigger event, these locations are used to adjust scan parameters during corresponding times after a subsequent trigger event 84 during a time period 86 when the image acquisition occurs as shown generally by reference numeral 88. The arrows 90 generally indicate the adjustment of scan parameters using the device locations 80. The arrow 92 generally indicates the movement in time. Scan parameters can include a receiver frequency offset, a transmitter phase offset or a transmitter frequency offset to cause positional shifts in the acquired data in the frequency, phase and slice dimensions respectively.

Figure 4:
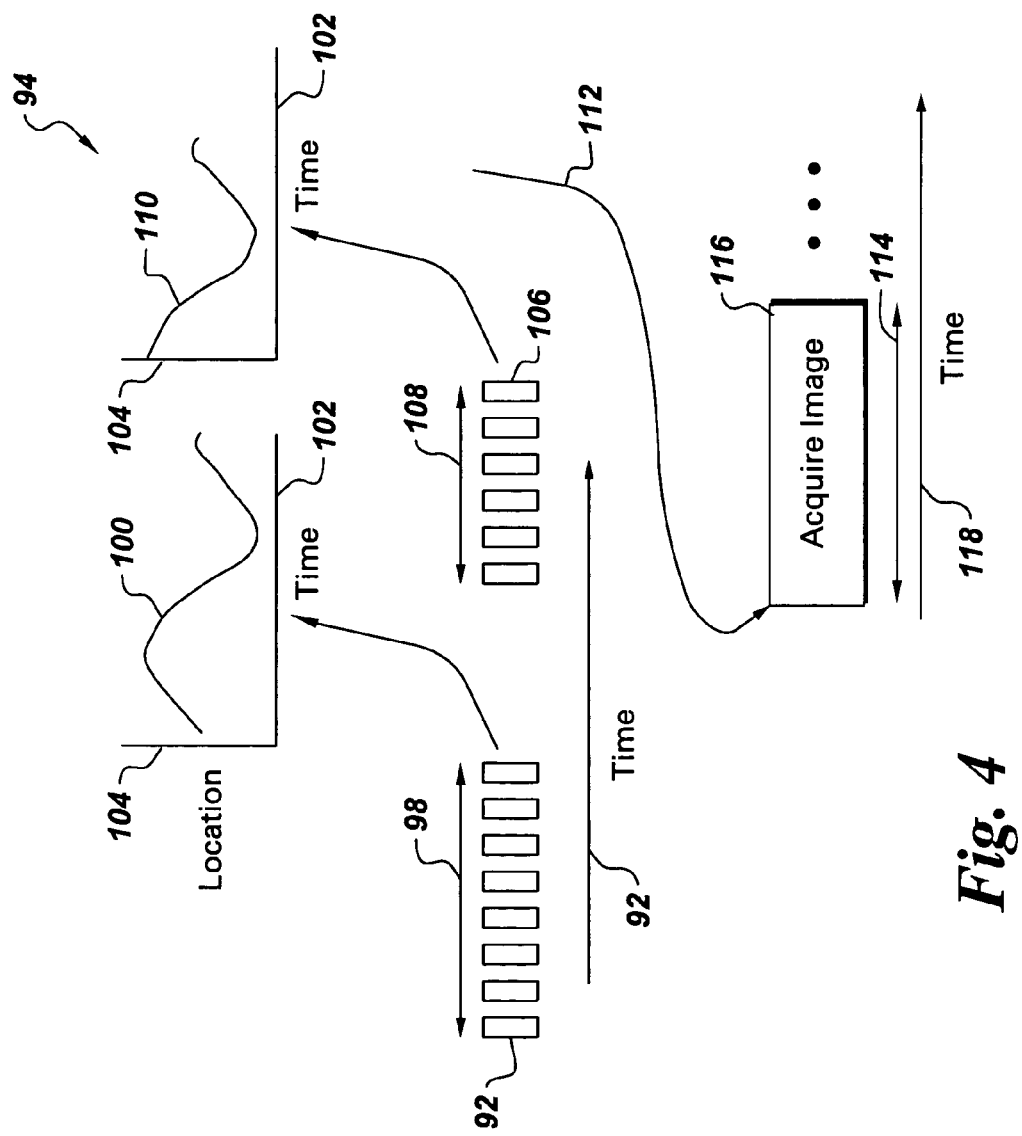
FIG. 4 is a diagrammatical representation illustrating another aspect of the method of FIG. 2 using an anatomic motion as a trigger to initiate the determination of the device location.

FIG. 4 similarly illustrates an alternate embodiment of the invention using an external trigger, for example the moving table, a mechanical actuator or a computer controlled action that is applied on the periodic movement of the anatomy. This technique can also be used for dynamic joint studies, where a full motion may be recorded and then a motion of interest can be revisited again. In this embodiment, at the first location sequence 96 for the device 32 (not shown) is initiated in synchrony with the external trigger over a period of time 98 and a positional information 100, is measured on a time 102 and a location 104 scale during the time period 98 and is saved. A second location sequence 106 is then initiated over a time period 108, and similarly the positional information 110 is collected over the time scale 102 and location scale 104. Data designated by reference numeral 110 from the period 108 is compared with the data collected in period 98 and used to determine the instantaneous position, designated generally by 112, during the periodic motion cycle. Once this is known, a scan is performed in period 114 using positions determined in period 98 and a dynamic image is acquired as shown generally by the reference numeral 116. The arrow 118 generally indicates the movement in time. The positional information as described herein would include the x and y co-ordinates and orientation component z, to precisely define the 3D space of the device. Additional rotational components with respect to time may also be acquired for greater accuracy.

Figure 5:
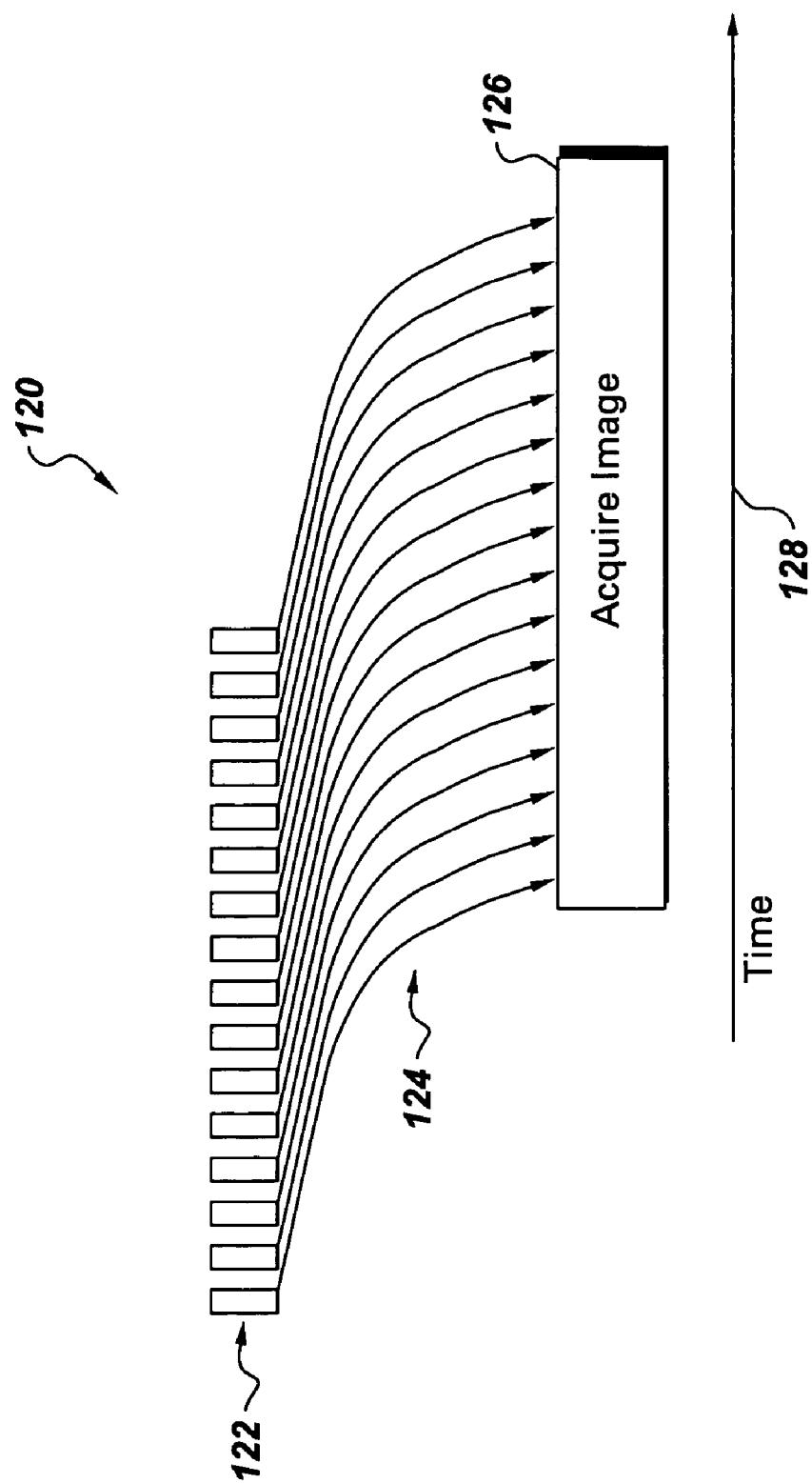
FIG. 5 is a diagrammatical representation of a further device tracking method of FIG. 2, where an anatomy of interest has a non-periodic motion.

FIG. 5 illustrates another exemplary time diagram, indicated generally by reference numeral 120 where the anatomy of interest (not shown) undergoes a non-periodic motion. Here interleaving is used for determining of the multiple device locations 122 with scanning 126 via adjusting 124 scan parameters using a respective device location. The arrow generally designated by reference numeral 128 indicates the movement in time. Thus in this embodiment, as the multiple device location is determined over a period of time (tracking), simultaneously image acquisition occurs for each respective device location. Thus the location measurements are interleaved with the views in the imaging sequence. In this embodiment gating may not be required, but the scan acquisition time may be stretched out if MR tracking is used for location determination since image acquisition and tracking are mutually exclusive.

It would be appreciated by those skilled in the art that, in the above described embodiments, since a one-to-one mapping between the locations measured during the first time period when the multiple device locations are determined, and the acquisition of views in a subsequent time period is not necessary, it is possible to interpolate the positional changes observed in first time period so that each view in the subsequent time period is acquired with a unique frequency, phase and slice offset.

The tracking method, as would also be appreciated by those skilled in the art may be an active tracking method such as MR tracking, RF tracking or optical tracking. Alternatively, the method can be a passive imaging method in which the location is determined by device visualization in conventional imaging. Although the aspects of present technique have been described with reference to MR imaging, the technique is equally relevant for other imaging modalities like ultrasound, computed tomography (CT), positron emission tomography (PET) and the like. Also aspects of present technique are applicable to interventional imaging using any of the above referenced modalities.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for tracking a device used in an MR imaging system, the method comprising:
    placing a predetermined device at a predetermined position with respect to an anatomy of interest;
    determining a plurality of device locations in response to movement of the anatomy of interest for the predetermined device prior to acquiring an image;
    adjusting scan parameters at each imaging pulse repetition time associated with a basic pulse sequence necessary to acquire all imaging lines for an acquired image, the adjusted scan parameters based on the plurality of device locations; and
    acquiring a dynamically corrected image in response to the adjusted scan parameters, wherein the scan parameters are adjusted to provide an offset for at least one scan parameter.

2. The method of claim 1, wherein the step of determining a plurality of device locations further comprises using a trigger.

3. The method of claim 2, further comprising initiating at least a first trigger event and a second trigger event.

4. The method of claim 3, further comprising:
    determining a plurality of device locations for the predetermined device over a selected period of time idler the first trigger event; and
    adjusting scan parameters at each location using the plurality of device locations during the second trigger event.

5. The method of claim 4, wherein adjusting scan parameters allows obtaining a dynamically corrected image location during the second trigger event.

6. The method of claim 1, wherein each location for the plurality of device locations comprises at least a horizontal and a vertical co-ordinate of the predetermined device.

7. The method of claim 2, wherein using a trigger comprises using an anatomic motion for triggering a first location sequence and a second location sequence.

8. The method of claim 7, further comprising:
    comparing the first location sequence and the second location sequence; and
    calculating an instantaneous location sequence over a predetermined period of time.

9. The method of claim 7, further comprising scanning by adjusting the scan parameters using the instantaneous location sequence.

10. The method of claim 1, wherein the anatomy of interest undergoes a periodic or a non-periodic motion.

11. The method of claim 10, further comprising interleaving the determining of the plurality of device locations with scanning via adjusting scan parameters using a respective device location.

12. The method of claim 1, further comprising comparing each location for the plurality of device locations to a pre-determined threshold.

13. The method of claim 12, further comprising suspending image acquisition when a device location from the plurality of device locations goes beyond the pre-determined threshold.

14. The method of claim 1, further comprising repeating the determining of the plurality of device locations a select number of times for signal averaging.

15. A method for tracking a device used in MR imaging system, the method comprising:
placing a predetermined device at a pre-determined position with respect to an anatomy of interest;
initiating at least a first trigger event and a second trigger event wherein said first trigger event is one of a physiological trigger or an external trigger and said second trigger event is one of a physiological trigger or an external trigger;
determining a plurality of device locations for the predetermined device in response to movement of the anatomy of interest over a selected period of time after said first trigger event and prior to acquiring an image, wherein said selected period for determining said plurality of device locations exceeds a period of said second trigger event;
adjusting scan parameters at each imaging tube repetition time (TR) associated with a basic pulse sequence necessary to acquire all imaging lines for an acquired image, wherein the scan parameters are adjusted during the second trigger event in response to the plurality of device locations prior to acquiring an image; and
acquiring a dynamically corrected image in response to the adjusted scan parameters, wherein the scan parameters are adjusted to provide an offset for at least one scan parameter.

16. The method of claim 15, wherein the anatomy of interest undergoes a periodic motion.

17. The method of claim 15, wherein adjusting scan parameters allows obtaining a dynamically corrected image location during the second trigger event.

18. A method for tracking a device used in MR imaging system, the method comprising:
determining a first location sequence in response to movement of an anatomy of interest for a predetermined device over a first period of time by a first trigger event prior to acquiring an image;
determining a second location sequence in response to movement of the anatomy of interest for the predetermined device over a second period of time by a second trigger event prior to acquiring an image, wherein said first trigger event and second trigger event is one of a physiological trigger or an external trigger and said first period of time exceeds said first trigger event;
comparing the first location sequence and the second location sequence prior to acquiring an image;
calculating an instantaneous location sequence based on comparing the first location sequence and the second location sequence over a pre-determined period of time prior to acquiring an image; and
scanning by adjusting the scan parameters which use the instantaneous location sequence, wherein the scan parameters are adjusted at each imaging pulse repetition time associated with a basic pulse sequence necessary to acquire all imaging lines for an acquired image, and further wherein the adjusted scan ameters based on the instantaneous location sequence.

19. The method of claim 18, wherein the external trigger is used for triggering the first location sequence and the second location sequence.

20. The method of claim 18, wherein the external trigger uses a periodic anatomic motion.

21. An MR imaging system comprising:
a predetermined device configured for placement at a pre-determined position with respect to an anatomy of interest;
a control and acquisition circuit configured for determining a plurality of device locations in response to a movement of the anatomy of interest prior to acquiring an image, and further configured for adjusting scan parameters at each imaging pulse repetition time associated with a basic pulse sequence necessary to acquire all imaging lines for an acquired image, wherein the adjusted scan parameters are based on the plurality of device locations and
a system controller circuit for acquiring a dynamically corrected image in response to the adjusted scan parameters, wherein the scan parameters are adjusted to provide an offset for at least one scan parameter; and said control and acquisition circuit is configured to use a trigger for initiating a determination of the plurality of device locations and said trigger is one of a physiological trigger or an external trigger.

22. The MR imaging system of claim 21, wherein the predetermined device is at least one of a guidewire, a catheter, an endoscope, a laparoscope, a biopsy needle, or a hand-held device.

* * * * *

UNITED STATES PATENT AND TRADEMARK OFFICE
CERTIFICATE OF CORRECTION

PATENT NO. : 7,787,935 B2  Page 1 of 1
APPLICATION NO. : 10/951300
DATED : August 31, 2010
INVENTOR(S) : Dumoulin et al.

It is certified that error appears in the above-identified patent and that said Letters Patent is hereby corrected as shown below:

In the Claims:

In Column 6, Line 44, in Claim 4, delete "idler" and insert -- after --, therefor.

In Column 7, Line 31, in Claim 15, delete "tube" and insert -- pulse --, therefor.

In Column 8, Line 19, in Claim 18, delete "ameters" and insert -- parameters --, therefor.

In Column 8, Line 37, in Claim 21, delete "locations" and insert -- locations; --, therefor.

Signed and Sealed this

Twelfth Day of October, 2010

David J. Kappos
*Director of the United States Patent and Trademark Office*